(12) United States Patent
Forrester et al.

(10) Patent No.: US 8,252,011 B1
(45) Date of Patent: Aug. 28, 2012

(54) MINIMALLY INVASIVE TECHNIQUE FOR PERFORMING PLANTAR FASCIOTOMIES AND SURGICAL INSTRUMENT FOR USE IN SUCH A TECHNIQUE

(75) Inventors: Perry C. Forrester, Houston, TX (US); Larry Weatherford, Houston, TX (US); Fred D. Youngswick, Novato, CA (US); Daniel F. Alberts, San Francisco, CA (US)

(73) Assignee: OsteoMed LLC, Addison, TX (US)

( * ) Notice: Subject to any disclaimer, the term of this patent is extended or adjusted under 35 U.S.C. 154(b) by 1204 days.

(21) Appl. No.: 11/536,961

(22) Filed: Sep. 29, 2006

Related U.S. Application Data

(63) Continuation of application No. 10/419,590, filed on Apr. 21, 2003, now abandoned.

(51) Int. Cl.
  *A61B 17/32* (2006.01)
(52) U.S. Cl. ........................ 606/167; 606/172
(58) Field of Classification Search .............. 606/52, 606/83, 164, 167, 170, 172, 205–208; 227/180.1, 227/175.2, 176.1; 30/280, 282, 286
  See application file for complete search history.

(56) References Cited

U.S. PATENT DOCUMENTS

| | | | |
|---|---|---|---|
| 3,750,671 A | 8/1973 | Hedrick | 606/172 |
| 3,967,377 A * | 7/1976 | Wells | 30/320 |
| 4,962,770 A | 10/1990 | Agee et al. | 128/898 |
| 5,029,573 A | 7/1991 | Chow | 128/4 |
| 5,253,659 A | 10/1993 | McNamara et al. | 128/898 |
| 5,269,290 A | 12/1993 | Barrett et al. | 128/4 |
| 5,273,024 A | 12/1993 | Menon et al. | 128/4 |
| 5,323,765 A | 6/1994 | Brown | 128/4 |
| 5,325,883 A | 7/1994 | Orr | 128/898 |
| 5,387,222 A | 2/1995 | Strickland | 606/167 |
| 5,387,223 A | 2/1995 | Agee et al. | 606/167 |
| 5,429,117 A | 7/1995 | McNamara et al. | 128/4 |
| 5,458,598 A | 10/1995 | Feinberg et al. | 606/52 |
| 5,472,448 A | 12/1995 | Marinoff et al. | 606/172 |
| 5,472,488 A | 12/1995 | Allman | 106/287.16 |
| 5,578,051 A | 11/1996 | Mirza | 606/170 |
| 5,611,808 A | 3/1997 | Hossain et al. | 606/170 |
| 5,613,976 A | 3/1997 | Agee et al. | 606/150 |
| 5,620,446 A | 4/1997 | McNamara et al. | 604/79 |
| RE35,525 E | 6/1997 | Stefanchik et al. | 606/139 |
| 5,636,779 A | 6/1997 | Palmer | 227/175.2 |
| 5,649,946 A | 7/1997 | Bramlet | 606/167 |
| 5,651,790 A | 7/1997 | Resnick et al. | 606/167 |
| 5,653,713 A | 8/1997 | Michelson | 606/83 |
| 6,179,852 B1 * | 1/2001 | Strickland et al. | 606/167 |

* cited by examiner

*Primary Examiner* — Tuan V Nguyen
(74) *Attorney, Agent, or Firm* — Baker Botts L.L.P.

(57) ABSTRACT

A surgical instrument includes a clamp having a handle with a pair of substantially parallel prongs or tines extending from the handle, all formed as a unitary body or article of manufacture. The handle and prongs define a channel to receive a knife. The knife includes a handle, a scalpel, and an extension arm coupling the scalpel to the handle. The clamp defines a minor image about a central axis. In this way, the surgeon need not concern himself with whether the knife is oriented properly within the channel. Also, the extension arm of the knife includes graduations to assist the surgeon in predetermining precisely the distance of cut in using the instrument. The upper prong of the clamp includes a downwardly extending capture pad having a bottom surface substantially parallel to the inner surface of the lower prong. The upper and lower prongs define a mouth, having a continuously increasing distance between upper and lower prongs so that the clamp is guided onto the tissue target of choice in a non-invasive manner.

9 Claims, 3 Drawing Sheets

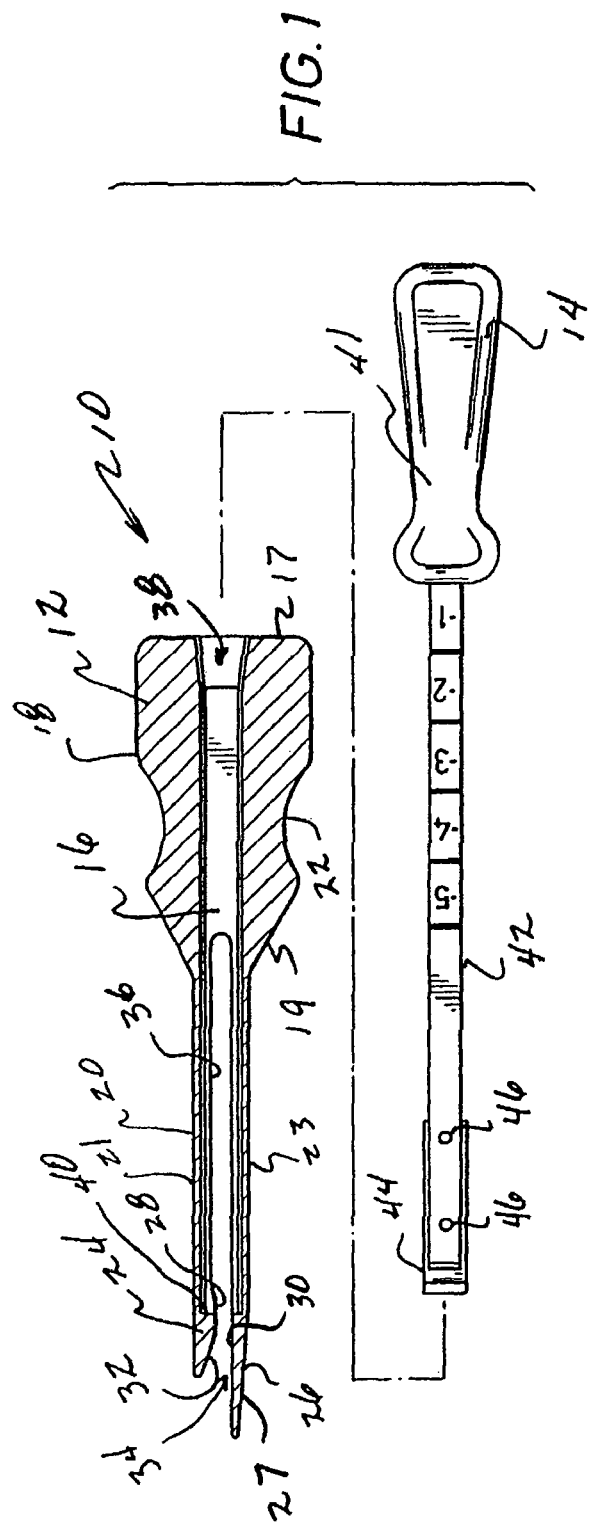
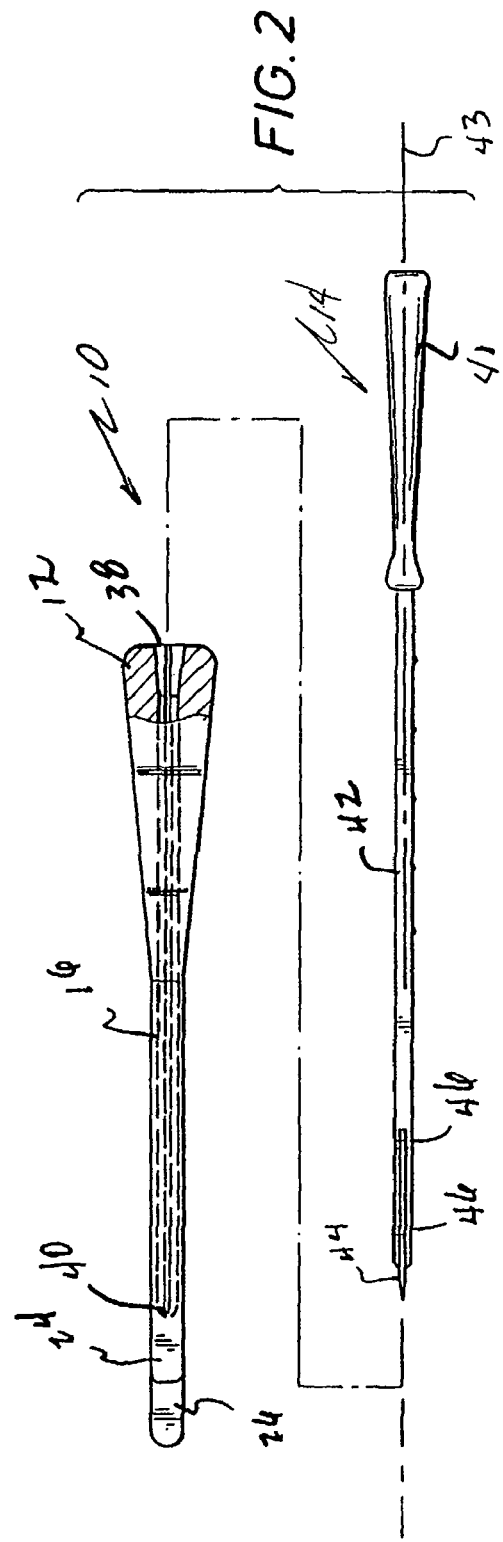
FIG.1
FIG.2

MINIMALLY INVASIVE TECHNIQUE FOR PERFORMING PLANTAR FASCIOTOMIES AND SURGICAL INSTRUMENT FOR USE IN SUCH A TECHNIQUE

RELATED APPLICATIONS

This application is a continuation of U.S. application Ser. No. 10/419,590, filed Apr. 21, 2003 and entitled "MINIMALLY INVASIVE TECHNIQUE FOR PERFORMING PLANTAR FASCIOTOMIES AND SURGICAL INSTRUMENTS FOR USE IN SUCH A TECHNIQUE.", which is abandoned.

FIELD OF THE INVENTION

The present invention relates generally to the field of surgical instruments, and, more particularly, to a technique and a surgical instrument for performing plantar fasciotomies.

BACKGROUND OF THE INVENTION

Chronic heel pain is one of the most common types of pain affecting the human body. It is estimated that over six million people in the United States develop this condition every year. Traditional treatments for such chronic heel pain include cortisone injections, oral anti-inflammatory medications, shoe inserts, and physical therapy. If such conservative treatments do not provide relief to the patient, surgery is often the only effective treatment.

The most common cause of heel and arch pain is a condition called plantar fasciitis (heel pain). This is an inflammation of a thick, fibrous band of tissue, called the plantar fascia, that runs along the arch of the foot from the heel to the toes, and aids in stabilization of the arch during walking and running. Symptoms may involve one or both of the arch and the inside heel area.

Plantar fasciitis is caused by a mechanical imbalance in the foot called pronation. Over-pronation causes the foot to roll in towards the arch and big toe area. The plantar fascia inserts in the heel bone and then spreads out and joins the toes. When the foot rolls in (pronates) the plantar fascia must try and stretch, but it cannot. Therefore, the fascia pulls at its insertion at the heel bone. In extreme cases, this pulling Causes plantar fasciitis, a painful and often debilitating condition.

There have been numerous studies reporting various success rates for conservative care treatments for chronic heel pain. Even with the high success rate of conservative care, a percentage of heel pain patients eventually become surgical candidates. Historically, a wide range of "open" techniques have been used to perform plantar fasciotomies. More recently, endoscopic techniques, which can be performed through one or two small incisions, have been used to perform less invasive plantar fasciotomies. Studies of these endoscopic techniques have shown a substantial reduction in post-operative morbidity and amount of time needed to return to normal activities when compared to traditional "open" techniques.

One such endoscopic technique for the performance of plantar fasciotomies is shown and described by McNamara et al. in U.S. Pat. No. 5,620,446. The device shown in the '446 patent includes a cutting instrument with a knife blade with a palpation end to sever tissue without snagging while palpating underlying tissue. The instrument comprises an elongated shaft having proximal and distal ends, a handle secured to the proximal end for use in manipulating the instrument, and the distal end having a generally blunt forward portion extending at an angle from the shaft and including an excising portion generally facing the proximal end of the shaft. In using the instrument, a sleeve is driven into the patient's foot from a medial aspect to a lateral aspect of the heel, i.e. entirely through the patient's foot. Visualization is made through the use of an arthroscopic camera, which is introduced through an open end of the sleeve on the medial aspect of the foot. The other open end of the sleeve is used as a working portal for the introduction of various surgical instruments to operate caudally on the line of insertion.

While this technique may have advantages over previous, more invasive techniques, it still requires incisions on both sides of the heel, and the sleeve must be large enough to accommodate both the camera and the cutting instrument, which in itself creates a trauma to the patient's foot and heel. Further, the instrument is expressly designed for the entire excision of the plantar fascia. It is known that excision part way, for example half way, through the plantar fascia is often sufficient for the complete relief of the patient's chronic heel pain.

Barrett et al., in U.S. Pat. No. 5,269,290, describe an endoscopic plantar fasciotomy procedure to relieve the symptoms of heel spur syndrome. A small, vertical incision is made in the medial side of the foot, and the adipose tissue is spread. A fascial elevator is inserted into the first incision to separate the plantar fascia from the surrounding tissue, creating a channel. A slotted canula and trocar are inserted into the channel, and a second incision is made on the lateral side of the foot, allowing the canula and trocar to substantially pierce the foot. The trocar is removed, and an endoscope is inserted into the canula through the medial portal. A cutting instrument is inserted into the lateral portal of the canula, and is used to release the plantar fascia from the heel bone. This procedure, like others in the art, suffer the drawbacks in that (1) incisions must be made on both sides of the foot; (2) the instruments must be made large enough to accommodate the endoscope; and (3) the instrument is designed to cut entirely through the plantar fascia, where cutting partially through the fascia would relieve the patient's pain.

Less invasive instruments have been proposed for other surgical techniques. For example, Strickland et al., in U.S. Pat. No. 6,179,852, describe a carpal tunnel device and method for carpal tunnel release surgery. However, the physiological structure in around the heel are quite different than those of the hand, and thus the capture clip is not well suited for the foot and heel. Further, as with the McNamara device, the Strickland instrument is used to completely divide the carpal ligament.

Thus, there remains a need for a technique and an instrument for performing plantar faciotomies that is less invasive than known techniques and instruments. The present invention is directed to such a technique and such an instrument.

Another source of chronic pain in the foot is Morton's neuroma. A neuroma is a benign tumor of a nerve. Morton's neuroma is not actually a tumor, but a thickening of the tissue that surrounds the digital nerve leading to the toes. It occurs as the nerve passes under the ligament connecting the toe bones (metatarsals) in the forefoot. Morton's neuroma most frequently develops between the third and fourth toes, usually in response to irritation, trauma, or excessive pressure. Treatment of this condition usually begins with shoewear adaptations. Sometimes simply moving to a wider shoe will reduce or eliminate the symptoms. An injection of xylocalne and cortisone into the area may help temporarily. If this fails to resolve the pain, surgery may be suggested. Surgery has traditionally involved removing the neuroma, and since the neuroma is part of the nerve, the nerve is removed as well. This results in permanent numbness in the area supplied by the nerve. Thus, there remains a need for a surgical instrument and a technique for treating Morton's neuroma which would eliminate the necessity of removing the neuroma, and therefor the nerve. The present invention is also directed to satisfying this need in the art.

SUMMARY OF THE INVENTION

This new minimally invasive approach allows the surgeon to safely and accurately incise the plantar fascia through a small single incision by achieving the accuracy and efficiency of endoscopy with the simplicity of an open approach. Therefore, the surgeon can utilize a set of minimally invasive instruments to isolate and incise a predetermined amount of the plantar fascia without any intrinsic tissue damage. The plantar fascia can be easily incised through a small vertical incision, e.g. ¾ cm.

The instrument of the invention comprises a self-adjusting clamp having a handle with a pair of substantially parallel prongs or tines extending from the handle, all formed as a unitary body or article of manufacture. The handle and prongs define a channel to receive a knife. The knife comprises a handle, a scalpel, and an extension coupling the scalpel to the handle. One advantage of the knife adapted for use in the clamp is that it defines a mirror image about a central axis. In this way, the surgeon need nor concern himself with whether the knife is oriented properly. Also, the extension arm of the knife includes graduations to assist the surgeon in predetermining precisely the distance of cut in using the instrument.

The upper prong of the clamp includes a downwardly extending capture pad having a bottom surface substantially parallel to the inner surface of the lower prong. This feature assists the surgeon in precisely locating the instrument on the plantar fascia, or on other ligaments of interest. Further, the upper and lower prongs define a mouth, having a continuously increasing distance between upper and lower prongs so that the clamp is guided onto the tissue target of choice in a non-invasive manner.

These and other features and advantages of this invention will be readily apparent to those skilled in the art.

BRIEF DESCRIPTION OF THE DRAWINGS

So that the manner in which the above recited features, advantages and objects of the present invention are attained and can be understood in detail, more particular description of the invention, briefly summarized above, may be had by reference to embodiments thereof which are illustrated in the appended drawings.

FIG. 1 is a side section view of a self-adjusting clamp and a side view of a knife insertable into the clamp in the performance of the technique of this invention.

FIG. 2 is a top view of a clamp in partial section and a top view of a knife insertable into the clamp.

DETAILED DESCRIPTION OF PREFERRED EMBODIMENTS

Figure 3:
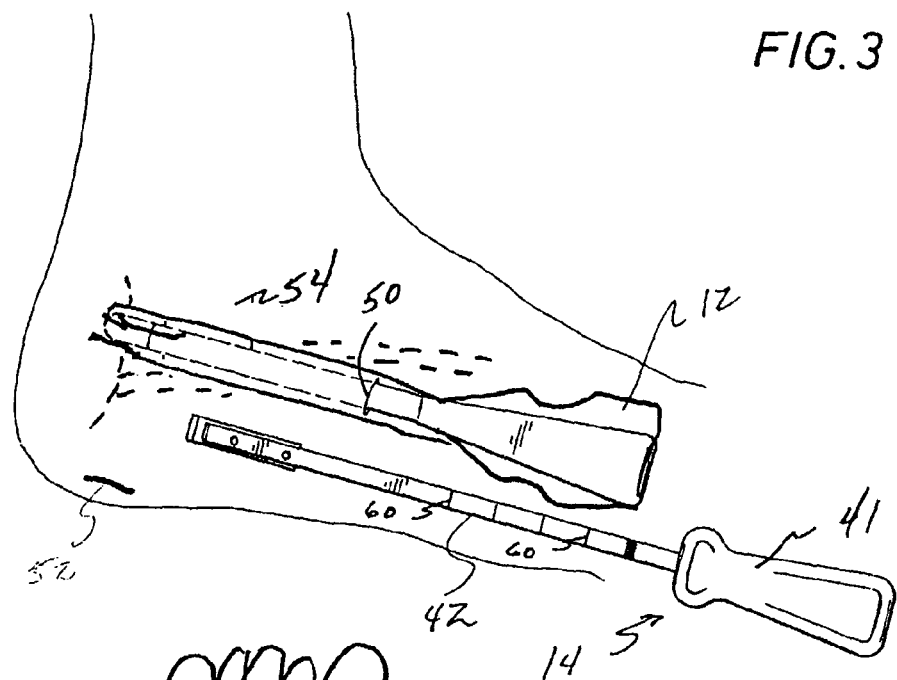
FIG. 3 is a perspective view of the clamp and knife as it is inserted into a patient's foot from a medial aspect.

So that the principles of the present invention may be better understood, the presently preferred embodiments of the invention will now be described in detail. It is to be understood, however, that no limitation of the scope of the invention is thereby intended, such alterations, modifications, and further applications of the principles of the invention being contemplated as would normally occur to one skilled in the art to which the invention relates.

FIGS. 1 and 2 depict a surgical device 10 constructed in accordance with one embodiment of the present invention. The device 10 includes a ligament clamp or sheath 12 and a knife 14. The ligament clamp 12 may be made out of spring steel, stainless steel, plastic, or any combination of the three, but is preferably made of stainless steel in upper and lower halves (not shown) and welded together to form a unitary body and then machined to make the clamp 12 as shown in FIGS. 1 and 2, a feature of the present invention. Portions of the knife 14 may be made from stainless steel. As shown and described below in respect of FIGS. 3, 4, and 5, the knife 14 slides through a central guide channel 16 of the clamp 12, to incise the selected ligament held within the clip 12.

The clamp 12 comprises primarily a handle or body portion 18 and a prong portion 20, formed as a unitary article of manufacture. The body portion 18 includes a proximal end 17 and a distal end 19. The handle portion 18 includes an ergonomic grip 22 to assist the surgeon in manipulating the device. The prong portion 20 includes an upper prong 24 and a lower prong 26. The lower prong 26 defines an angled surface 27, which in use of the instrument helps to avoid the clamping of tissue other than the target ligament. The upper prong 24 defines a capture pad 28 having a tissue gripping surface, which is substantially parallel to an upper surface 30 of the lower prong. Thus, the capture pad extends from the upper prong toward the lower prong in order to grip tissue between the prongs.

Extending laterally from the surface 28 is an angled face 32, thereby creating a mouth 34 having a continuously increasing clearance distance between the upper and lower prongs, another feature of the invention. Further, the surface 28 runs parallel to a bottom surface 36 of the upper prong, and is lower than the surface 36. These features of the present invention enable the surgeon to palpate the tissues surrounding the plantar fascia and precisely position the device, thereby eliminating the need for any endoscopic equipment. These features also minimize the damage during surgery of tissues surrounding the surgical site. Note also that the upper prong has an upper surface 21 that is substantially parallel to a lower surface 23 of the lower prong.

Another feature of the present invention resides in the fact that the distance between the prongs, indeed the distance between the capture pad and the upper surface of the lower prong is self-adjusting. The mouth 34, defined in part by the surface 32, moves onto and on either side of the target ligament, and as the capture pad rides up onto the ligament, the prongs move apart to accommodate the ligament. The distance between the capture pad and the upper surface of the lower prong is typically about 2 mm, and as the clamp is moved onto the plantar fascia, for example, the distance can spread to 6-8 mm, for example. Further, because the surface 32 is preferably located on the upper prong, the upper prong tends to flex more than the upper prong. This feature of the invention adjusts the instrument to differing thickness of fascia or other ligaments, and pushes other, surrounding tissue out of the way.

The central guide channel 16 of the clamp defines a mouth 38 where the knife 14 is inserted into the clip 12. The channel 16 then extends through the handle portion 18 and into the clip portion 20, terminating in a stop 40.

The knife 14 comprises primarily a handle 41, a graduated extension arm 42, and a scalpel 44, preferably attached to the arm 42 as with rivets 46, although other appropriate attachments may be used. The arm 42 includes a scale, preferably marked in centimeters, to assist the surgeon in precisely cutting the target ligament a predetermined distance.

In FIG. 2, note that the knife 14 is oriented longitudinally along a centerline 43. Furthermore, each half of the knife 14, on either side of the centerline 43, is a mirror image of the other half. Thus, the knife may be reversed and still fit within the central guide channel 16, another feature of the present invention.

Now that the structure of the surgical instrument of the present invention has been described in detail, the device will now be described in its intended environment of performing surgical procedures.

Procedure for Plantar Fasciotomy

Figure 4:
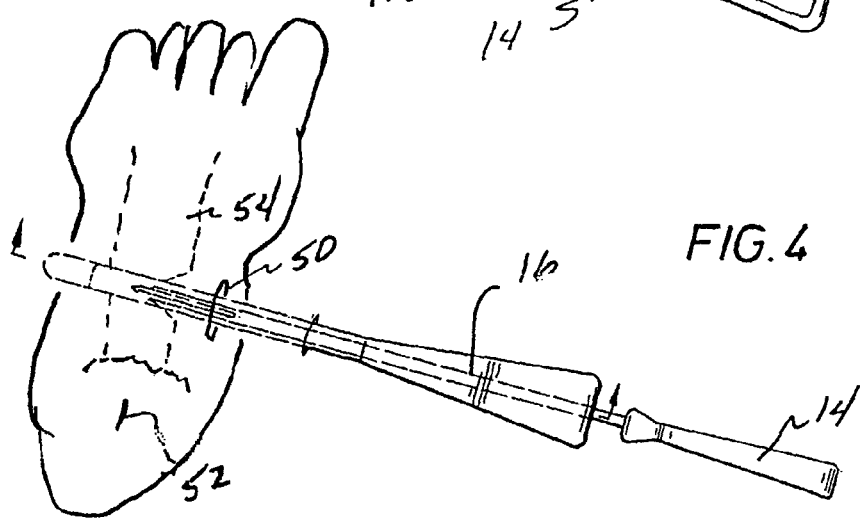
FIG. 4 is a perspective view of the clamp and knife, illustrating partial incision of the plantar fascia.
Figure 5:
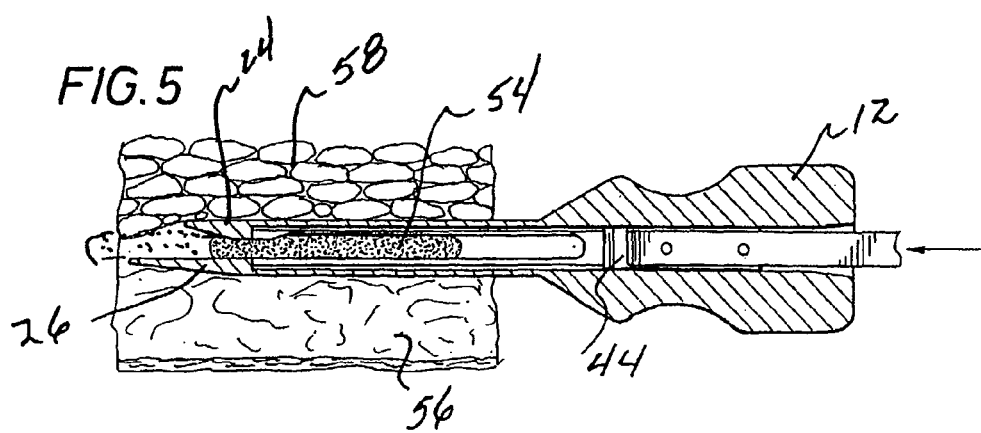
FIG. 5 is a side section view of the clamp and knife with surrounding tissues during the performance of the technique of this invention.

FIGS. 3 through 5 depict the use of the instrument of this invention in performing a plantar fasciotomy. While the following description is directed to plantar fasciotomy, the same procedural steps may be used in incising the Achilles tendon. Prior to inserting the instrument of this invention, the surgeon first prepares the surgical site. The surgeon begins site preparation by palpating the medial tuberosity of the calcaneous plantarly. An incision 50 is then made about 1 cm distal from that point. A centerline 52 is then marked along the bottom of the patient's heel with a surgical marker. Preferably, using a #15 blade, the ¾ cm to 1 cm vertical incision 50 is made at the medial aspect of the heel just distal to the origin of the medial band of the plantar fascia 54, with the incision starting approximately one centimeter from the plantar aspect of the heel and ending well below the neurovascular bundle.

Utilizing small curved Metzenbaum scissors (not shown), the incision is deepened to start a plane of approximately one centimeter under the plantar fascia 54 and dorsal to the subcutaneous tissue 56, as shown in FIG. 5. A small, slightly curved tool (not shown) is then used to extend the plane across to the lateral aspect of the plantar fascia. Another tool, referred to as a fascia separator and constructed in a manner similar to the clamp, is then introduced to separate the plantar fascia 54 from both plantar and dorsal surrounding tissue. This tool has an upper and lower prong separated by a 5 mm gap. The lower prong extends approximately ½ inch farther than the upper prong to allow for initial palpation of the underside of the fascia before introduction and capture of the plantar fascia.

After removal of the separator, the clamp 12 of this invention is introduced and positioned securely around the plantar fascia using the same palpation technique used previously with the tissue locator and fascia separator. The position of the clamp around the plantar fascia is most clearly shown in FIG. 5. The design allows for isolation of the plantar fascia and protects the surrounding soft tissue structure 56 and 58 from damage during the procedure. The longer, lower prong 26 of the device is plantar to the fascia and the short upper prong 24 is dorsal. The slotted channel 16 extends throughout the handle and passes throughout the length of the device allowing the passage of the blade 14 while incising only the enclosed fascia. The calibrated extension arm or shaft 42 of the knife 14 is marked with 0.5 centimeter graduated increments 60 that are used as a reference point to the proximal end of the handle when the blade is placed on the bottom of the foot in the position needed to make the desired length of cut.

The knife 14 is then placed into the device, as shown in FIG. 4, and pushed toward the lateral aspect of the foot, with negative pressure and as the foot is dorsi-flexed until it reaches the previously determined calibrated mark. The surgeon can feel resistance and hear the distinct sound of the plantar fascia being incised. Note in FIG. 4 that the incision has been made partway through the fascia to a predetermined extent. The clamp and the knife are then removed and the incision is closed with one or two interrupted sutures. Prior to closing the incision, the tissue locator, previously described, can be reintroduced to palpate for any remaining uncut fibers of the plantar fascia 54.

Procedure for Intermetatarsal Nerve Decompression

Figure 6:
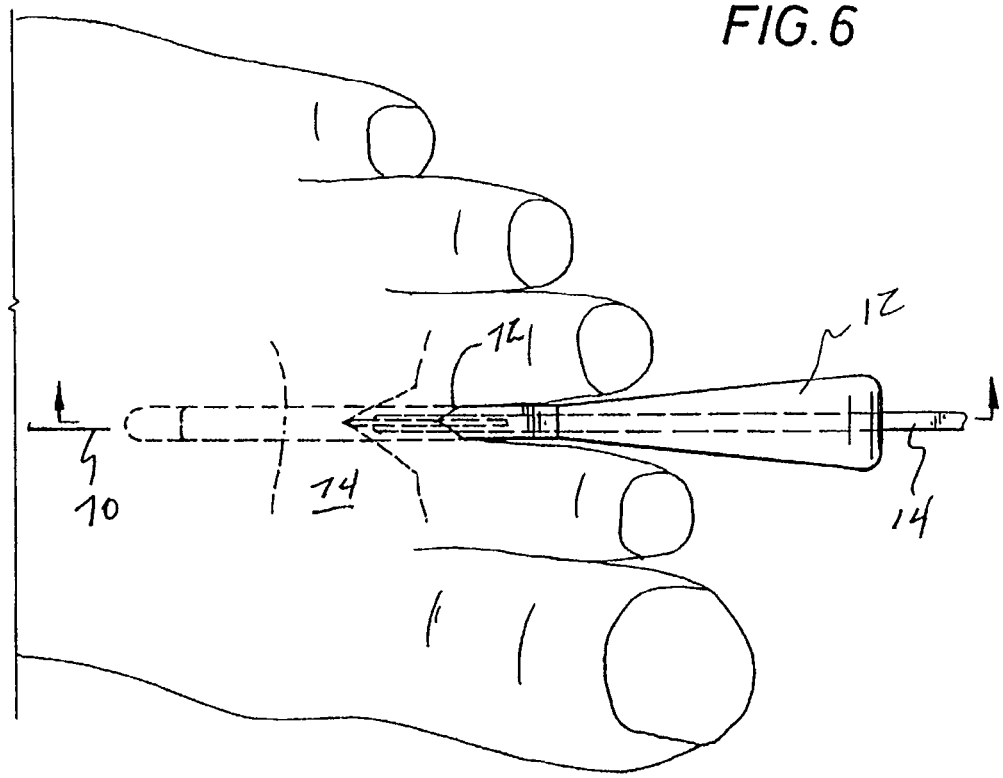
FIG. 6 is a top view of the instrument of this invention severing a transverse metatarsal ligament.
Figure 7:
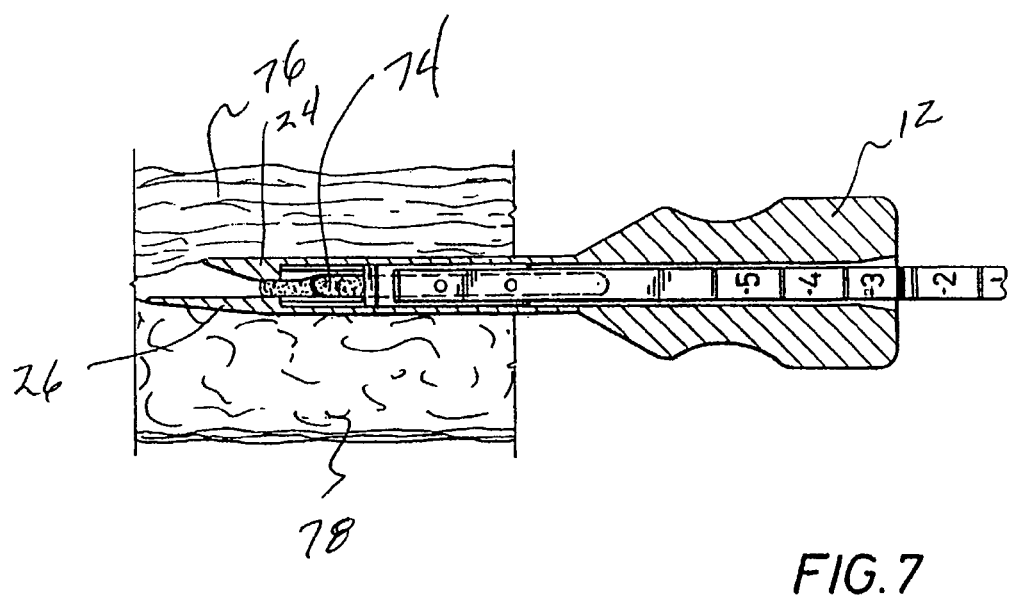
FIG. 7 is a side view of the clamp and knife with surrounding tissues while severing a transverse metatarsal ligament.

The surgical instrument of this invention is also particularly adapted for the performance of intermetatarsal nerve decompression to relieve Morton's Neuroma. This procedure using the present invention is shown in FIGS. 6 and 7. Using a straight edge instrument (not shown), a pre-surgical mark 70 is made paralleling the metatarsal heads in order to define the correct path for introduction of the clamp and preparatory instruments. Using a #15 blade, a 7 mm vertical incision 72 is made in the web space. This incision is made vertically to protect the neurovascular bundle to the toe. A small curved Metzenbaum scissor (not shown) is then used to palpate and create a small plane on the plantar aspect of the transverse intermetatarsal ligament (TIML) 74. The tissue locator, previously described, is then used to create a plane across the underside of the ligament 74. Care is taken to ensure that all instruments are introduced in a paralleling manner to the adjacent metatarsals. The separator is then introduced in order to separate the TIML 74 from surrounding tissue 76 and 78 and to create planes plantar and dorsal to the TIML for proper placement of the device. As previously described, the separator has a upper and lower prong separated by a 5 mm gap. The lower prong extends approximately 0.5 inch further than the upper prong to allow for initial palpation of the underside of the ligament before introduction and capture of the TIML.

After removal of the separator, the clamp 12 is then introduced and positioned securely around the ligament 74 using the same palpation technique used previously with the tissue locator and separator. Note that the capture pad moves beyond the ligament 74 and that the entire ligament is to be incised in this procedure. Thus, no measuring of a predetermined distance of cut is required, as in the previously described plantar fascia procedure. The device design allows for isolation of the TIML and protects the nerve and surrounding soft tissue structures 76 and 78 from damage during the procedure. The longer, lower prong 26 of the device is plantar to the ligament and the short upper prong 24 is dorsal. The knife is then introduced into the channel 16 to incise only the enclosed TIML.

Once the device is properly positioned, the knife 14 is then introduced into the slotted channel to allow for a controlled cut which can be predetermined using the measurements of the blade extension arm or shaft. While the blade is passing throughout the slotted channel, the surgeon can feel resistance and hear the ligament being incised. The clamp and knife are then removed. The tissue locator can then be reintroduced to palpate between the metatarsal heads for confirmation of the successful release. Then, the incision is closed with one or two interrupted sutures.

The principles, preferred embodiment, and mode of operation of the present invention have been described in the foregoing specification. This invention is not to be construed as limited to the particular forms disclosed, since these are regarded as illustrative rather than restrictive. Moreover, variations and changes may be made by those skilled in the art without departing from the spirit of the invention.

We claim:
1. A surgical device, comprising:
   a. a clamp comprising:
      i. a body defining a proximal end, a distal end, and a central guide channel therethrough;
      ii. a lower prong extending from the distal end of the body a first length; and
      iii. an upper prong extending from said distal end of the body a second length and generally parallel to the lower prong, the first length longer than the second length, the lower and upper prongs defining a mouth having a continuously increasing clearance distance therebetween, the upper prong comprising a capture pad extending from the upper prong toward the lower prong, the capture pad comprising a tissue gripping surface and being adapted to grip between itself and the lower prong, a ligament being incised; and
   b. a knife adapted to be slideably received through said central guide channel and between said upper prong and said lower prong, wherein the knife comprises a handle, a scalpel, and an extension arm coupling the scalpel to the handle, the extension arm having graduations thereon.

2. A surgical device, comprising:
   a. a clamp comprising:
      i. a body defining a proximal end, a distal end, and a central guide channel therethrough;
      ii. a lower prong extending from the distal end of the body a first length; and
      iii. an upper prong extending from said distal end of the body a second length and generally parallel to said lower prong, the first length longer than the second length, the upper prong defining a capture pad extending from the upper prong toward the lower prong, the capture pad comprising a tissue gripping surface and being adapted to grip between the upper and lower prongs, a ligament being incised;
      wherein the upper prong defines an upper surface, the lower prong defines a lower surface, and wherein the upper surface of the upper prong comprises a middle interior surface that is parallel to a corresponding middle interior surface of the lower prong, the middle interior surface and the corresponding middle interior surface adapted to contact the ligament being incised; and
   b. a knife adapted to be slideably received through said central guide channel and between said upper prong and said lower prong.

3. The device of claim 2, wherein the clamp is formed as a unitary article of manufacture.

4. The device of claim 3, wherein the lower and upper prongs define a mouth having a continuously increasing clearance distance therebetween.

5. The device of claim 2, wherein the knife comprises:
   a. a handle;
   b. a scalpel; and
   c. an extension arm coupling the scalpel to the handle, the extension arm having graduations thereon.

6. The device of claim 2, wherein the knife defines a longitudinal centerline, and wherein the knife defines mirror images on either side of the centerline.

7. The device of claim 2, wherein the central guide channel extends into the upper and lower prongs.

8. The device of claim 7, further comprising a stop in the central guide channel extension in the upper prong.

9. A surgical device, comprising:
   a. a clamp comprising:
      i. a body defining a proximal end, a distal end, and a central guide channel therethrough, the body comprising a top surface and a bottom surface, the top and bottom surface each being contoured to facilitate gripping, the proximal end being generally flat, and the central guide channel defining an opening adapted to receive a knife;
      ii. a lower prong extending from the distal end of the body a first length, the lower prong defining a tip and an angled surface extending therefrom; and
      iii. an upper prong extending from said distal end of the body a second length and generally parallel to the lower prong, the first length longer than the second length, the lower and upper prongs defining a mouth having a continuously increasing clearance distance therebetween, the upper prong comprising a capture pad extending from the upper prong toward the lower prong, the capture pad comprising a tissue gripping surface and being adapted to grip between itself and the lower prong, a ligament being incised;
      iv. wherein the upper prong defines an upper surface, the lower prong defines a lower surface, and wherein the upper surface of the upper prong comprises a middle interior surface that is parallel to a corresponding middle interior surface of the lower prong;
      v. the central guide channel extending into the upper and lower prongs, the central guide channel extension in the upper prong comprising a stop; and
      vi. the clamp being formed by welding together an upper and a lower half, each half being stainless steel; and
   b. the knife adapted to be slideably received through said central guide channel and between said upper prong and said lower prong, the knife comprising:
      i. a handle;
      ii. a scalpel; and
      iii. an extension arm coupling the scalpel to the handle with a plurality of rivets, the extension arm being marked with 0.5 centimeter graduated increments; and
      iv. a longitudinal centerline wherein the knife defines mirror images on either side of the centerline.

* * * * *